(12) United States Patent
Yang et al.

(10) Patent No.: US 7,771,569 B2
(45) Date of Patent: Aug. 10, 2010

(54) ENRICHMENT OF LIGHT HYDROCARBON MIXTURE

(75) Inventors: Dali Yang, Los Alamos, NM (US); David Devlin, Santa Fe, NM (US); Robert S. Barbero, Santa Cruz, NM (US); Martin E. Carrera, Naperville, IL (US); Craig W. Colling, Warrenville, IL (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 12/469,552

(22) Filed: May 20, 2009

(65) Prior Publication Data

US 2009/0236213 A1 Sep. 24, 2009

Related U.S. Application Data

(63) Continuation of application No. 11/266,123, filed on Nov. 3, 2005, now abandoned.

(60) Provisional application No. 60/664,800, filed on Mar. 23, 2005.

(51) Int. Cl.
*B01D 3/00* (2006.01)
*B01D 15/00* (2006.01)

(52) U.S. Cl. .............. 203/39; 210/640; 95/50

(58) Field of Classification Search .......... 210/640, 210/634–637; 95/45, 46, 50, 52, 44, 43; 96/11; 585/818, 654; 203/99, 39; 55/524
See application file for complete search history.

(56) References Cited

U.S. PATENT DOCUMENTS

| | | | | |
|---|---|---|---|---|
| 3,758,605 A | * | 9/1973 | Hughes et al. ............. | 585/818 |
| 4,614,524 A | * | 9/1986 | Kraus ........................... | 95/50 |
| 5,062,866 A | * | 11/1991 | Ho .............................. | 95/50 |
| 5,107,059 A | * | 4/1992 | Chen et al. .................. | 585/818 |
| 5,332,424 A | * | 7/1994 | Rao et al. .................... | 95/47 |
| 5,472,607 A | * | 12/1995 | Mailvaganam et al. ...... | 210/490 |
| 5,670,051 A | * | 9/1997 | Pinnau et al. ............... | 210/651 |
| 5,773,844 A | * | 6/1998 | Kawamura et al. ......... | 257/57 |
| 5,954,858 A | * | 9/1999 | Peretti et al. ............... | 95/44 |
| 6,039,792 A | | 3/2000 | Calamur et al. | |
| 6,271,319 B1 | * | 8/2001 | Baker et al. ................. | 526/68 |
| 6,309,550 B1 | | 10/2001 | Iversen et al. | |
| 6,316,684 B1 | * | 11/2001 | Pinnau et al. ............... | 585/818 |
| 6,361,582 B1 | * | 3/2002 | Pinnau et al. ............... | 95/45 |

OTHER PUBLICATIONS

Lawson et al., "Membrane Distillation," Journal of Membrane Science, Feb. 1997, vol. 24, No. 1, pp. 1-25.

(Continued)

*Primary Examiner*—Ana M Fortuna
(74) *Attorney, Agent, or Firm*—Samuel L. Borkowsky

(57) ABSTRACT

Light hydrocarbon enrichment is accomplished using a vertically oriented distillation column having a plurality of vertically oriented, nonselective micro/mesoporous hollow fibers. Vapor having, for example, both propylene and propane is sent upward through the distillation column in between the hollow fibers. Vapor exits neat the top of the column and is condensed to form a liquid phase that is directed back downward through the lumen of the hollow fibers. As vapor continues to ascend and liquid continues to countercurrently descend, the liquid at the bottom of the column becomes enriched in a higher boiling point, light hydrocarbon (propane, for example) and the vapor at the top becomes enriched in a lower boiling point light hydrocarbon (propylene, for example). The hollow fiber becomes wetted with liquid during the process.

1 Claim, 17 Drawing Sheets

U.S. PATENT DOCUMENTS

| | | | | |
|---|---|---|---|---|
| 7,067,597 | B2* | 6/2006 | Van Egmond et al. | 526/68 |
| 7,250,545 | B2* | 7/2007 | Roman et al. | 585/818 |
| 7,399,897 | B2* | 7/2008 | Roman et al. | 585/818 |
| 7,479,227 | B2* | 1/2009 | Da Costa et al. | 210/640 |
| 2009/0236213 | A1* | 9/2009 | Yang et al. | 203/39 |

OTHER PUBLICATIONS

Gabelman et al., "Hollow Fiber Membrane Contactors," Journal of Membrane Science, Jul. 1999, vol. 159, No. 1, pp. 61-106.

Zhang et al., "Hollow Fibers as Structured Distillation Packing," Journal of Membrane Science, Apr. 2003, vol. 215, No. 1-2, pp. 185-193.

Cussler, "Nonselective Membranes for Separations," J. Chem. Technol. Biotechnol., vol. 78, Feb. 2003, pp. 98-102.

Chung et al., "Distillation With Nanoporous or Coated Fibers," Journal of Membrane Science, vol. 257, Jul. 2005, pp. 3-10.

Yang, et al., "Designing Hollow-Fiber Contactors," AIChE Journal, Nov. 1986, vol. 32, No. 11, pp. 1910-1916.

* cited by examiner

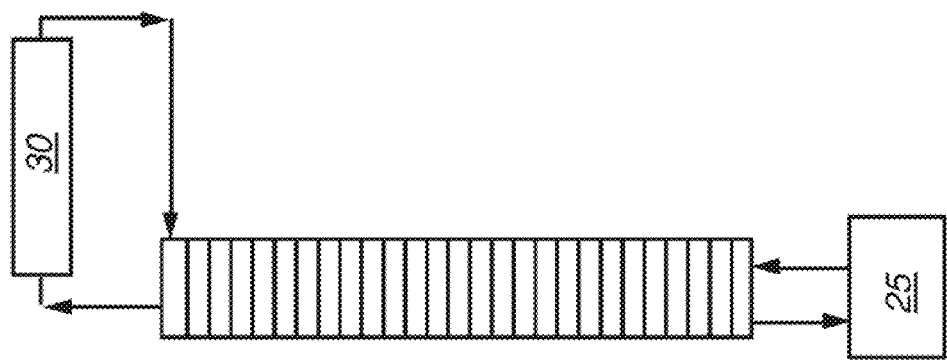
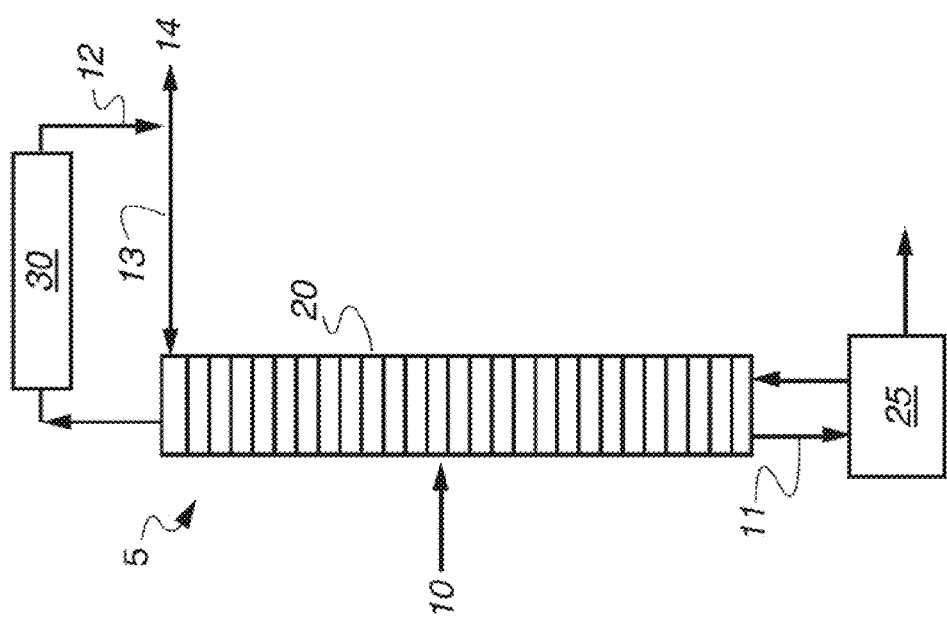

ENRICHMENT OF LIGHT HYDROCARBON MIXTURE

RELATED APPLICATIONS

This application is a continuation of U.S. patent application Ser. No. 11/266,123 filed Nov. 3, 2005, now abandoned entitled "Porous Membrane Materials as Structured Packing for Distillation," which claims the benefit of provisional application No. 60/664,800 filed on Mar. 23, 2005, titled "Porous Membrane Materials as Structured Packing for Distillation", all hereby incorporated by reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to enrichment of a light hydrocarbon mixture using a distillation column.

BACKGROUND OF THE INVENTION

The petroleum industry uses 6.9 quadrillion BTU's of energy per year, 40% of this energy is used for distillation nation wide. The energy consumption used in the distillation process is even larger worldwide. Ethylene and propylene (olefins) are two of the largest commodity chemicals in the U.S. and are major building blocks for the petrochemicals industry. These olefins are mostly separated by cryogenic distillation that demands extremely low temperatures and high pressures. Over 75 billion pounds of ethylene and propylene are distilled annually in the U.S. at an estimated energy requirement of 400 trillion BTU's.

The largest potential area for energy reduction is in the cryogenic isolation of the product hydrocarbons from the reaction by-products, methane and hydrogen. This separation requires temperatures as low as $-150°$ F. and pressures exceeding 450 psig.

Light hydrocarbon olefin/paraffin separations are dominated by cryogenic distillation technology at an estimated $1.2 \times 10^{14}$ BTU's expended annually. In addition, there is enormous capital and operating costs associated with distillation. This has motivated an appreciable amount of effort towards pursuing alternative olefin/paraffin separation technologies. In the past decade, reactive or selective membranes for the olefin and paraffin separation had been widely investigated. However, the difficulty of long term stability associated with these facilitated transport membranes is a major obstacle.

Recently, the possibility of capillary condensation using a porous structure to separate light gases was explored, and the potential of using non-selective membrane for the olefin/paraffin separation was shown (see U.S. Pat. No. 6,039,792). In 2003, work was reported on using non-selective and non-porous membrane as structured packing to replace the distillation column for water-isopropanol separation and also suggested the possibility of using this technology for light hydrocarbon mixture separations (reference: Zhang, G. et al., "Hollow fibers as structured distillation packing," Journal of Membrane Science 2003, 215, 185-193).

Non-selective micro-porous membranes have been used as a barrier material in membrane contactors for vapor/liquid or liquid/liquid mass transfer, desalination, concentrating fruit juice and enriching the oxygen in blood during open-heart surgery (reference: "Hollow fiber membrane contactors", Journal of Membrane Science, 159 (1999) 61-106).

A unique feature of micro-porous membranes is a large surface area within a small volume, normally more than 3000 $m^2/m^3$, that provides an increased rate of mass transfer at least 10-20 times faster than the conventional tray and structured packing materials (creating an intimate contact between liquid and vapor phases). Although the high efficient Sulzer Chemtech® structured packing materials (AG Corporation), such as 250 Y/X, have conquered the chemical industry globally in the past twenty years, it has not been used in the $C_3$ and $C_4$ splitters since they require high liquid loads where structured packings typically deteriorate in performance. An advantage of using hollow fibers as structured packing is that the liquid and vapor velocity are not interrupted by the two-phase fluid mechanics. Therefore, the column packed with hollow fibers can operate above the normal flooding limits and below the normal loading limits.

However, the general requirement for use of a porous membrane in membrane distillation is that the membrane should not be wetted by the process liquids, because it is believed that the membrane wall once filled with liquid will increase the mass transfer resistance between the liquid and vapor phase, as well as reduce the flux of process fluid passed through the membrane wall. Therefore, historically it has been a requirement that the membrane used in the membrane distillation exhibit non-wetting characteristics (reference: "Membrane distillation", K. W. Lawson et al., Journal of Membrane Science, 124 (1997) 1-25; "Hollow fiber membrane contactors", Journal of Membrane Science, 159 (1999) 61-106; and, "Designing hollow fiber contactors", M. C. Yang et al., AIChE Journal, 32 (1986) 1910-1916).

The present invention includes the uses of a non-selective mesoporous and/or microporous membrane to separate olefinic mixtures from light vapor byproducts at higher temperatures and lower pressures than are currently required.

Various objectives, advantages and novel features of the invention will be set forth in part in the description which follows, and in part will become apparent to those skilled in the art upon examination of the following or may be learned by practice of the invention. The objectives and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes an apparatus and method for use of distillation packing material made from a non-selective meso/microporous membrane that separates light hydrocarbon mixtures.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 5a is a schematic of a partial reflux distillation setup.

FIG. 5b is a schematic of a total reflux distillation setup.

DETAILED DESCRIPTION

The present invention includes the use of non-selective mesoporous and/or microporous fibers as structured packing for separation of light hydrocarbons like olefinic mixtures and olefin and paraffin mixtures. Microporous is defined as a material with pore size of less than 0.01 micrometer. Mesoporous is defined as a material with pore size in the micrometer range (a few hundred micrometers to 0.01 micrometer). Testing results prove that the hollow fiber made of non-selective mesoporous and/or microporous fibers can be used as structured packing, thus, allowing for an alternative technology for conventional distillation.

Non-selective mesoporous and/or microporous materials that may be used in this application include, but are not limited to: plastics (e.g. polypropylene, polysulfone, polyethylene, polyvinylididene, mixed ester, and polyestersulfone), ceramics, and metals. Preferred embodiments of these materials exhibit pore sizes that range from about 0.02 to a few hundred micrometers for fiber wall thicknesses ranging from about 30 to 500 micrometers, and, more precisely, when the pore size is less than about 0.05 micrometers the corresponding wall thickness should be less than about 100 micrometers. When the pore size is larger than a few micrometers, the corresponding fiber wall thickness is preferably thicker than 100 micrometers.

The use of hollow fiber material as structured packing overcomes flooding or loading concerns, and offers a wide range of operating conditions. Furthermore, the large mass transfer area provided by the hollow fibers increases separation efficiency and, therefore, reduces the operating and capital cost when compared to use of conventional distillation packing materials.

Figure 1:
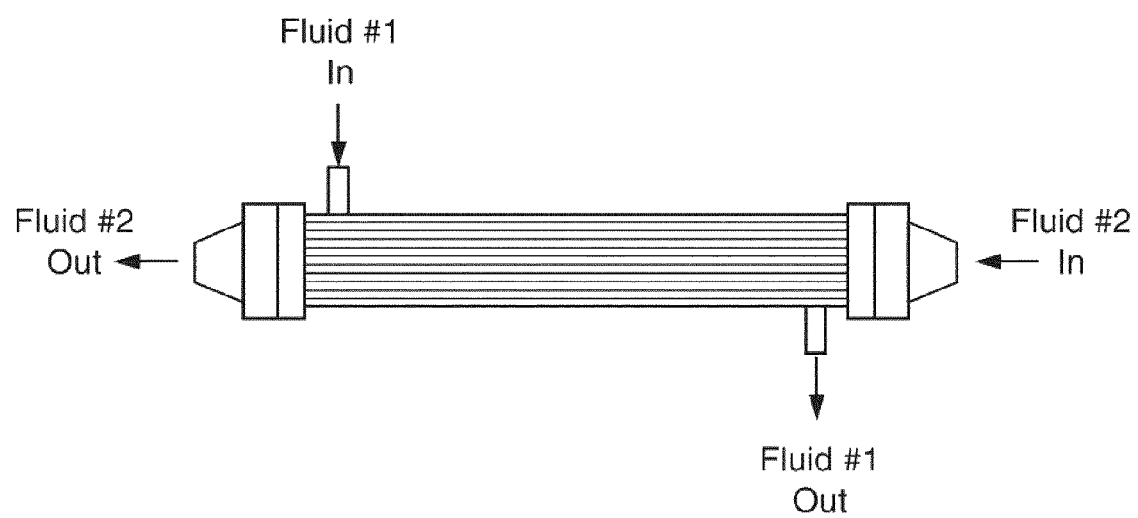
FIG. 1 is a pictorial illustration of a membrane contactor module.
Figure 2:
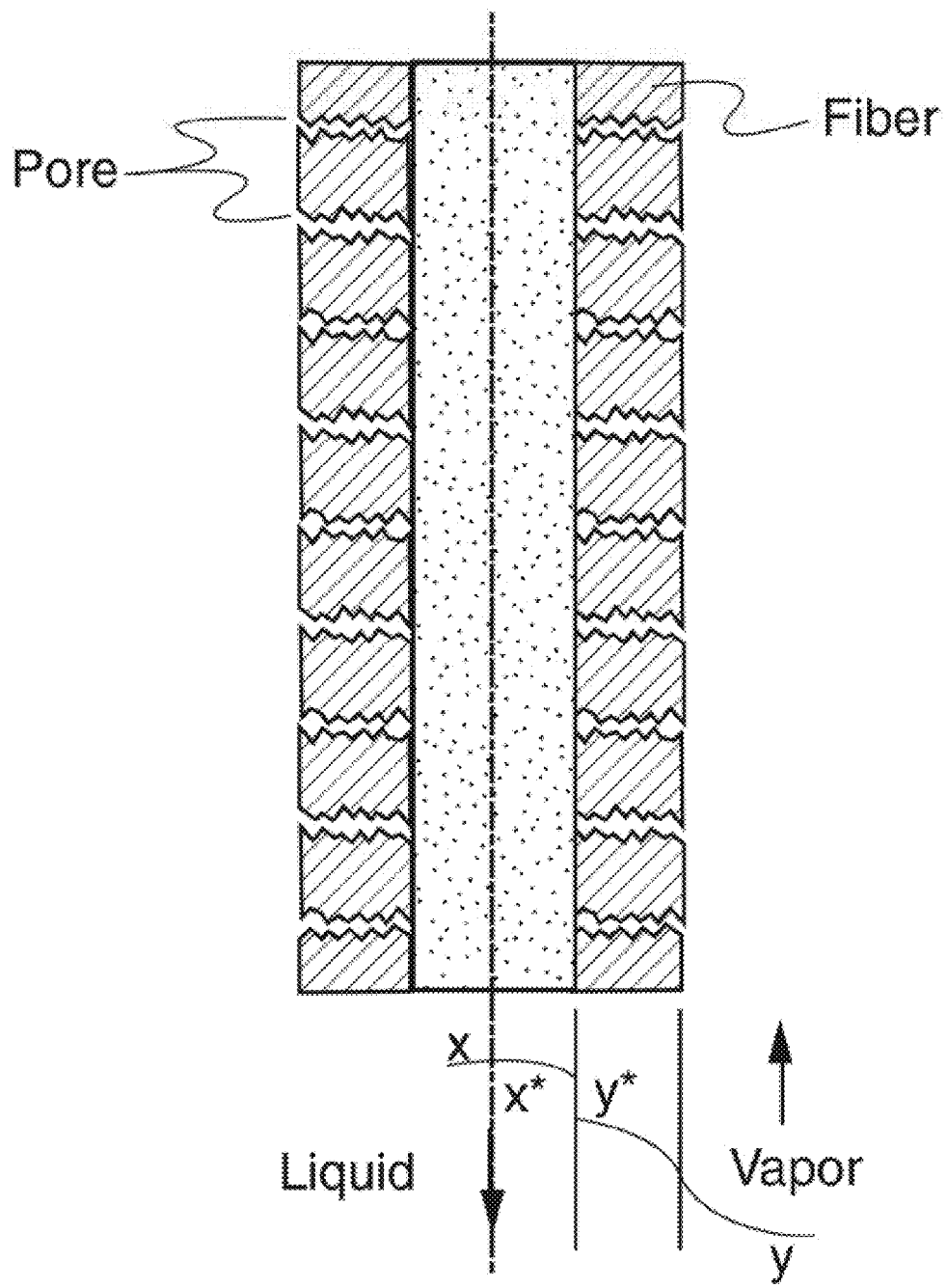
FIG. 2 pictorially shows the concentration profile change across a non-wetting membrane.

Referring to FIG. 1, when a membrane contactor is used for liquid/vapor separation, fluid #1 flows through the lumen side of the hollow fiber, and fluid #2 flows on the shell side of the hollow fiber. The liquid phase does not penetrate the pores in the membrane. Referring now to FIG. 2, where X, X* are the mole fraction of volatile compounds in liquid phase at operational and equilibrium conditions, and Y, Y* are the mole fraction of more volatile compounds in vapor phase at operational and equilibrium conditions, the transport subject to more volatile species occurs by evaporation from the liquid phase into the pores of membrane at the pore mouth of the liquid side, followed by vapor molecules' diffusion across membrane to the opposite side. In this scenario, the equilibrium between liquid and vapor phases occurs at the pore mouth, along the membrane surface of the liquid side. The contact area is limited to the open pores on the surface to where liquid contacts. Typically, the pore sizes used in this type of membrane contactor ranges from 100 Å to 0.5 μm.

Figure 3A:
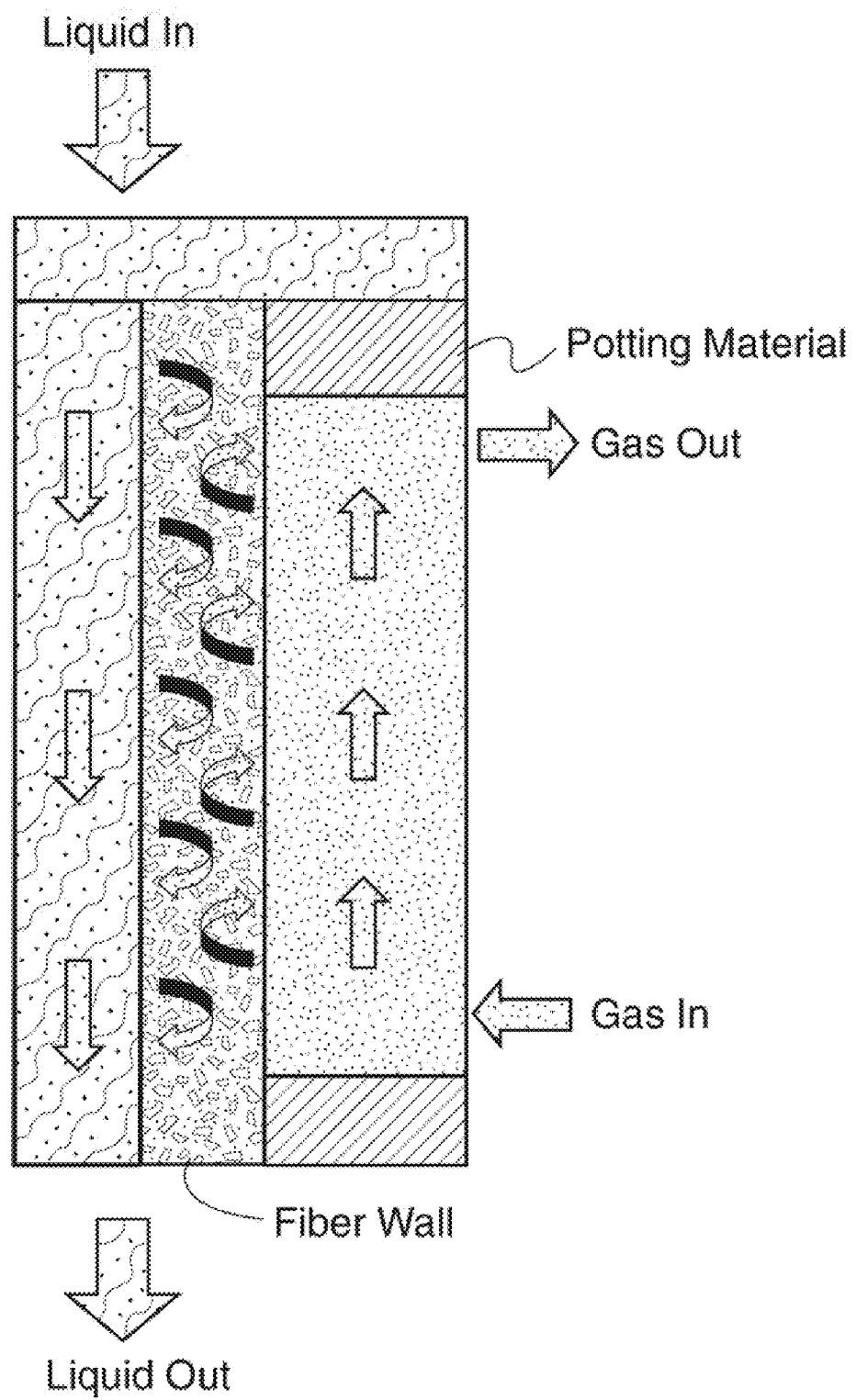
FIG. 3a pictorially illustrates the intimate contact between liquid and vapor within the wall of porous material used as structured packing.
Figure 3B:
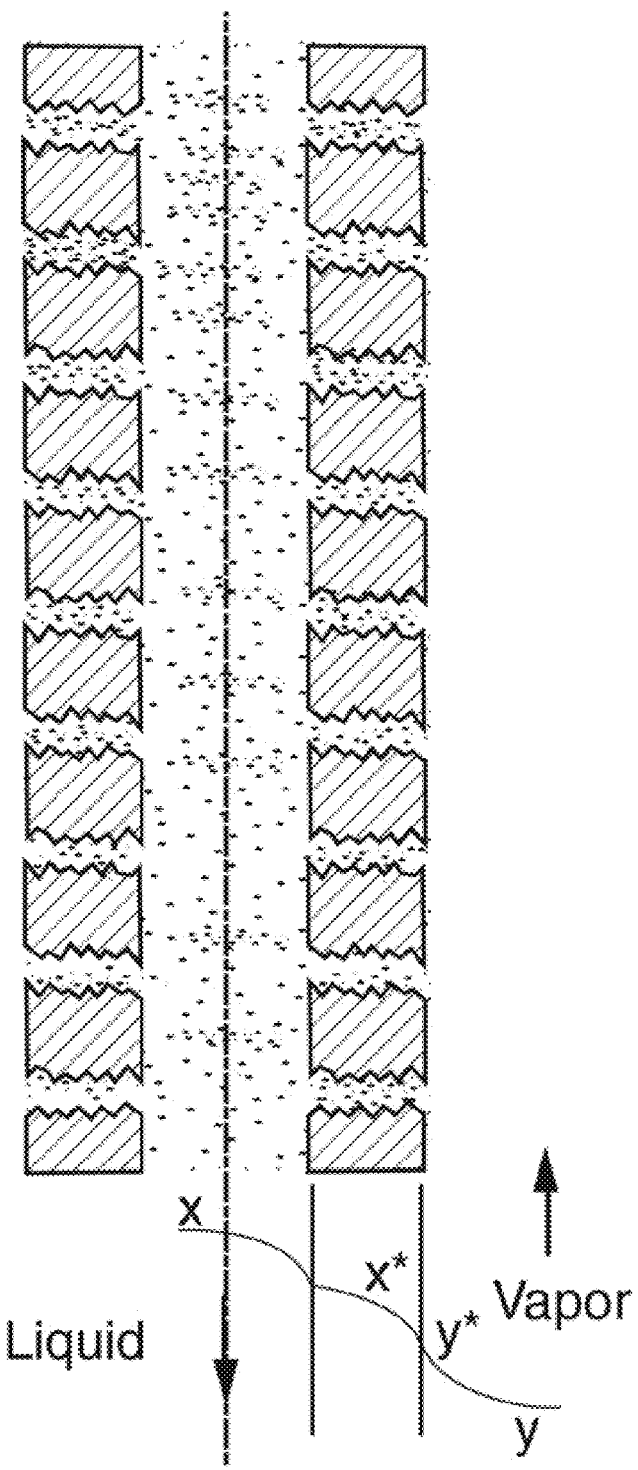
FIG. 3b pictorially illustrates the concentration profile change across a wetting membrane.

Referring to FIG. 3a, in the present invention, unlike the method above, the micro-porous materials in tube shape, e.g. hollow fiber used in this work, can be wetted with the process liquid (pores can filled with liquid (see FIG. 3b)). By judiciously selecting the morphology of porous membrane and controlling the pressure difference across the membrane, the penetration rate of liquid can be controlled and thus allow the liquid phase to form an ultra-thin film uniformly coating the curvature of the large pores (pore size on the vapor side of the membrane can be larger than 50 μm). This surface feature exists within the wall of the fiber at the boundary contacting with the vapor phase (see FIG. 3a).

Therefore, it is preferred that the asymmetric structures with a denser structure (pore size<0.5 μm) contacts the liquid phase while the open cellular foam structured (pore size ranges from 0.5 to several hundred micrometers) contacts the vapor phase. The more volatile species evaporates into the vapor phase at the boundary at the vapor side while the condensed phase flows downward on the membrane surface and/or inside the wall of the membrane.

Due to the wettibility of the porous materials, the liquid can penetrate through the entire membrane and thus ensures the full usage of the surface of the porous materials. Therefore, the mass transfer rate can be accelerated as the vapor flows through the curvature of the pores where the thin liquid film is covered to disturb the boundary layer of the vapor phase, thus reduce the resistance of mass transfer process.

A system for separating olefin/paraffin mixtures includes a fluid tight column and a porous material that divides the column into a liquid and vapor chamber. Inside the housing, the vapor and liquid counter-currently flow through both sides of the boundary materials that can be wetted with the process liquid. The vapor and liquid phases interact with each other either at the membrane surface contacting with vapor phase and/or inside the wall of the porous materials where the high boiling point material, e.g. paraffin in the olefin/paraffin mixture is condensed into the liquid phase and purer low boiling point material, e.g. olefin is left in the vapor phase (see FIG. 3a).

Although a great effort has been devoted to improve the uniformity of liquid fed across the column, the thickness of the liquid layer on the surface of the packing materials is difficult to control. The appreciable amount of channeling and maldistribution of liquid is always a limiting mass transfer process and thus reduces the separation efficiency of the packing materials. Also, there is not a clear boundary between the liquid and vapor phases; for example, even the widely used Sulzer Chemtech® structure packing material 250Y that provides high separation efficiency, has not been commercially utilized for propane and propylene mixture separation due to the difficulty of disengagement of the vapor from the liquid phase.

Figure 4:
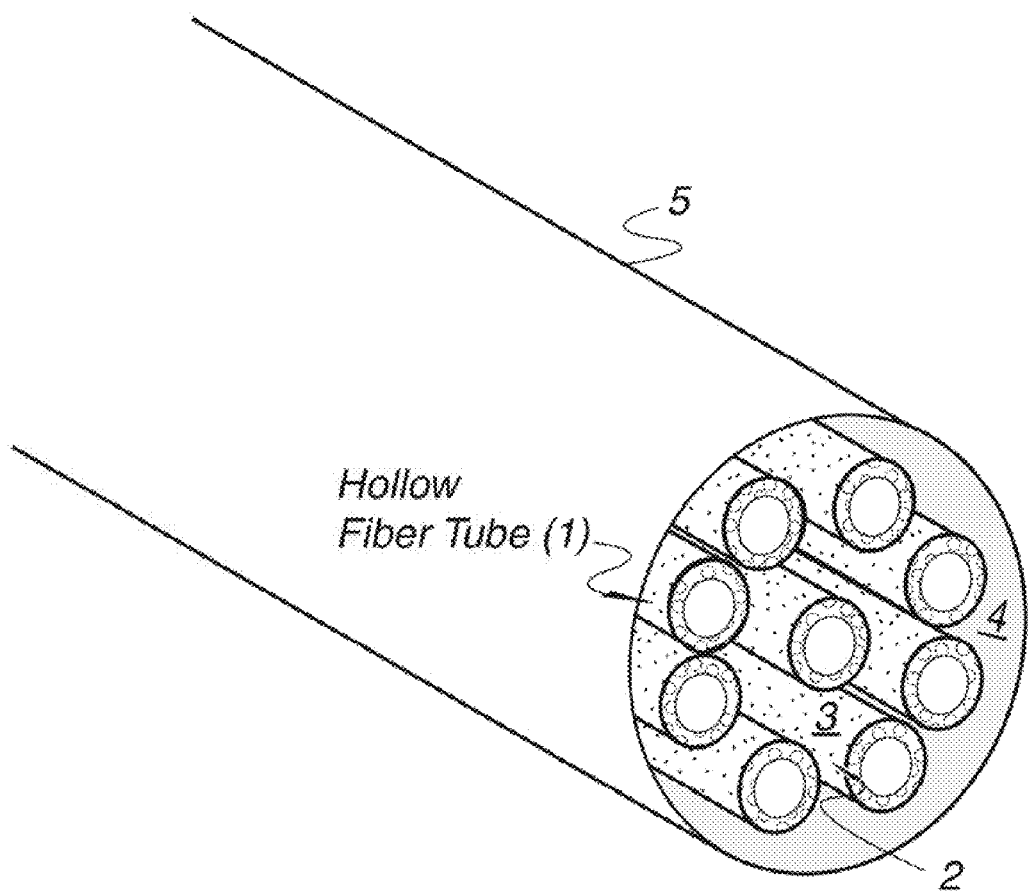
FIG. 4 pictorially illustrates parallel porous tubes within a distillation column.

However, referring now to FIG. 4, by using porous tubes 1 orientated in parallel inside column 5, liquid flows within porous tubes 1 while vapor flows counter currently within channels 2 that are defined by outside wall 3 of porous tubes 1 and column 5 inner wall 4. The liquid phase is evenly distributed and driven by the gravity flow downward inside the porous tube, the wettability of the porous materials allows the liquid to drain freely across the membrane while a thin film can be uniformly formed on the other side of the tube along the entire tube (where the liquid and vapor phases are contacting).

Experimental results show that the largest mass transfer coefficients (>0.01 cm/sec) are obtained with fibers containing large pores (<1 μm-30 μm) and exhibiting a thicker wall (up to 450 μm), which is consistent with the preceding discussion. The height equivalent to theoretical plate (HETP) using these fibers has been reduced to <20 cm when the liquid flux is up to 200 $m^3/m^3$-hr compared to values of >30 cm at the liquid flux less than 100 $m^3/m^3$-hr of Sulzer Chemtech® packing materials. In this work, the mass transfer surface area is about 500-2300 $m^2/m^3$. If the mass transfer area is larger than 3000 $m^2/m^3$, HETP's less than a few centimeters can obtain.

Since a large specific mass transfer area (a ($m^2/m^3$)>1000) is the inherent advantage of hollow fiber configuration, together with the enhanced mass transfer coefficient ($K_G$), the mass transfer time (1/$K_G$·a)—reciprocal of the product of mass transfer coefficient and the specific area can largely be reduced from >50 sec (for conventional packing materials) to <1 sec for the current design.

Distillation is the process of heating a liquid solution to drive off a vapor and then collecting and condensing the vapor. The separation mechanism is based on the difference in volatility of components in the mixture. Referring now to FIG. 5a, which shows typical distillation column 5, in a typical distillation process, feed solution 10 is fed into middle section 20 of column 5; high boiling point component 11 is concentrated and removed from reboiler 25 while low boiling point component 12 is collected after condenser 30. In order to increase the separation efficiency, partial amount 13 of low boiling point component 12 is returned back to column 5 with remaining distillate (final product) 14 routed to post-processing (not shown).

In evaluating a distillation process, it is convenient to assume a condition of total reflux (all the condensed liquid is returned to the column) as illustrated in FIG. 5b because this simplifies the operation on a pilot plant (or on a laboratory scale) by limiting continuous feed and withdrawl of distillate from the system, thereby reducing the difficulty of determining the height of a transfer unit (HTU) or HEPT for the packing materials used in the distillation process.

Figure 6:
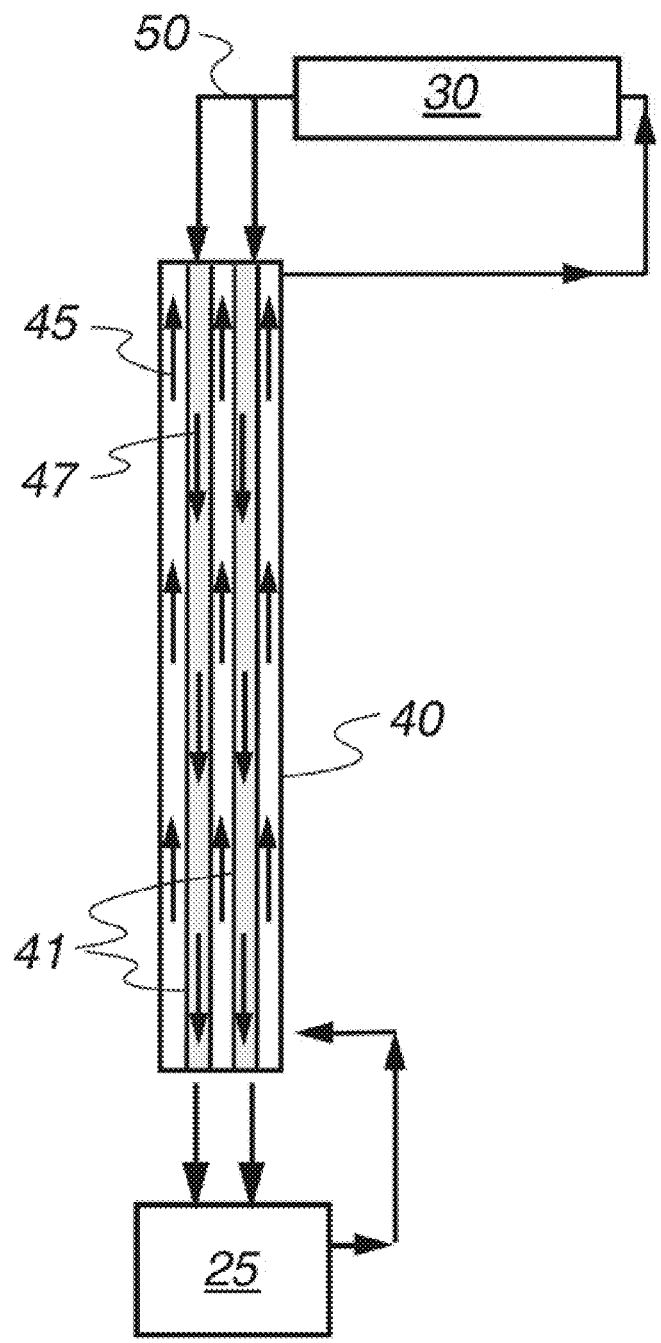
FIG. 6 is a schematic detailing liquid and vapor flow paths within a total reflux embodiment of the membrane distillation setup.

Referring now to FIG. 6, within hollow fiber distillation column 40, vapor 45 flows up the outside of hollow fiber 41 while liquid 47 flows down the inside of hollow fiber 41. The analysis of differential distillation is simplified when analyzing total reflux conditions. The overall mass balance between the vapor and liquid condensate at any point is simply:

$$G=L, \quad (1)$$

where G and L are the molar vapor and liquid flowrate in column 40. In a steady-state flow condition, Ö, G and L are constant. For the total reflux 50, Ö called the operation line on a MaCable-Thiele Diagram is simply:

$$x=y, \quad (2)$$

where x and y are the mole fraction of the more volatile species in the vapor and the liquid phase, respectively. For the mass balance on either vapor or liquid phase alone a column, the following equations apply:

$$0 = -G\frac{dy}{dz} + K_y a(y^* - y) \quad (3)$$

where $K_y$ is the overall vapor phase and liquid phase mass transfer coefficients, respectively, a is the mass transfer area ($cm^2/cm^3$), z is the distance measured from the bottom of the column, y is the mole fraction of the most volatile species in the vapor, and y* is the mole fraction in equilibrium with the liquid. Thus, the rate equations derived from the integrated form of Equation 3 is Equation 4:

$$l = \int_0^l dz = \frac{G}{K_y a} \int_{y_0}^{y_l} \frac{dy}{y^* - y} \quad (4)$$

Equations (4) may be written as:

$$l=HTU·NTU \quad (5)$$

where HTU is a height of a transfer unit defined as:

$$HTU = \frac{v_G}{K_G a} \quad (6)$$

and NTU is the number of transfer unit given by:

$$NTU = \int_{y_0}^{y_l} \frac{dy}{y^* - y} \quad (7)$$

In the petroleum industry, the height equivalent to a theoretical plate (HETP) is commonly used to replace HTU to express mass transfer capability for the structured packing materials in the distillation tower. The HEPT is related to the HTU through a linearization of operating and equilibrium curves expression as follows:

$$HETP = HTU * \frac{Ln(mG/L)}{mG/L - 1}, \quad (7)$$

where m is the slope of equilibrium curve. Since mG/L will change considerably throughout a distillation, the HETP will change as the composition changes, even the HTU may not. Therefore, HEPT, combining more factors than HTU, is widely accepted by the fractionation researchers.

Figure 7:
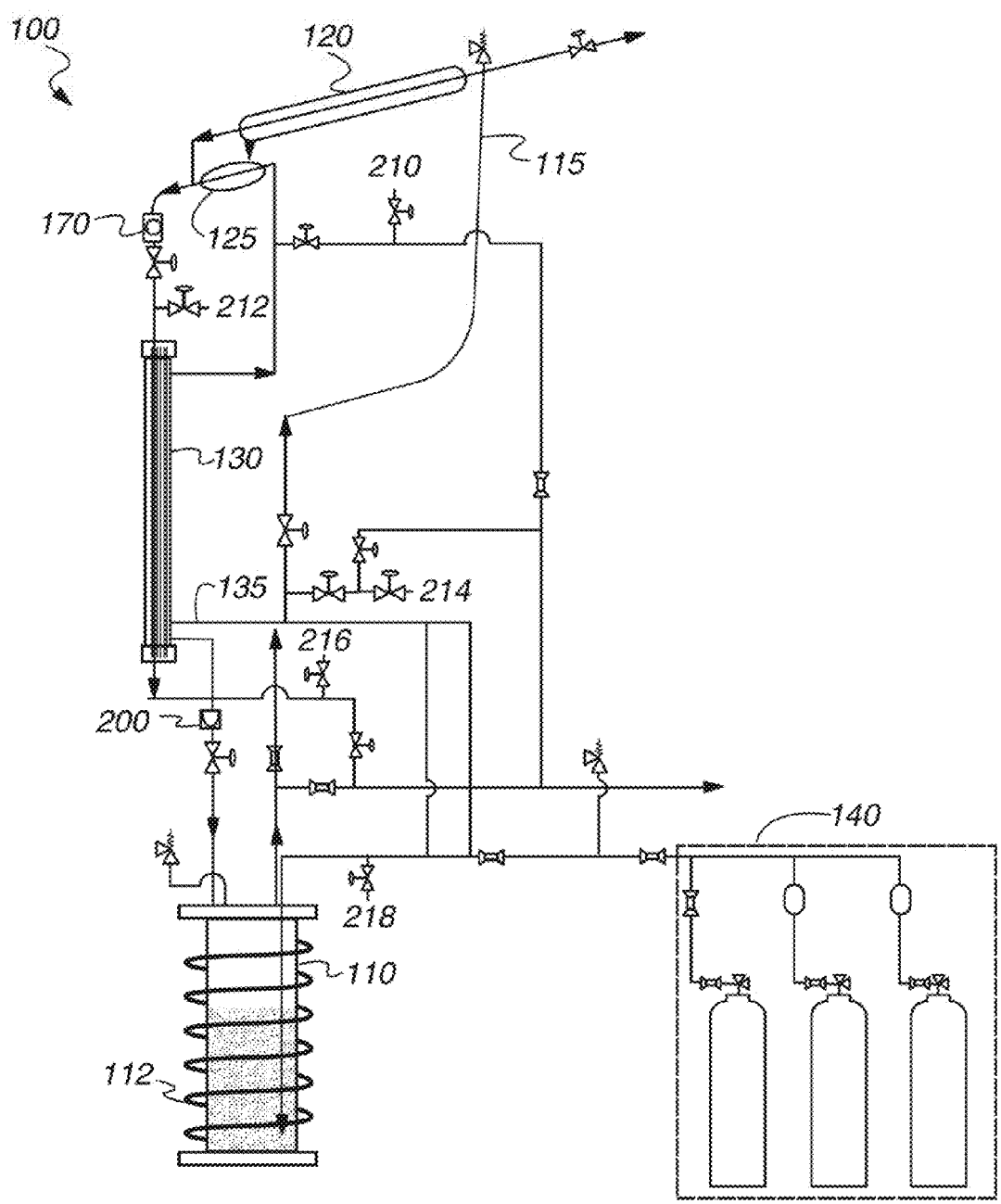
FIG. 7 is a schematic detailing the test setup of the present invention.

Referring to FIG. 7, there were three major components for the distillation system 100 in which the experiments were carried out: reboiler 110, condenser 120, and membrane module 130. Vapor supply system 140 was used to initially charge reboiler 110 with starting materials. Five sampling stations 210, 212, 214, 216, and 218, were used to monitor the vapor and liquid composition at different sections of system 100 during operation. Heater/chiller system 112 was used to precisely control operating temperature during operation. Thus, by controlling the temperature difference between the heater and chiller, the liquid flow rate was controlled. Drain 135 was used to prevent liquid buildup on the vapor side. Bypass 115 was used to add liquid to reservoir 125 in preparation for initial startup.

View port 170, mounted between condenser 120 and the top of membrane module 130 was used to ensure that hollow fibers 40 were filled with liquid during the experiment. A rheonik coriolis meter 200 (Liquid controls, LLC), with RHM 03 sensor and RHE08-transmitter, was used to measure the liquid flow. As the system was working in a total reflux condition, the vapor flow rate was back calculated from the liquid flow based on the mass balance between the vapor and liquid flow.

During the experimental run, the vapor and liquid samples (~10 ml and 40 Psig) were collected into a sample bottle at the five sample stations. HP M series micro gas chromatograph (GC) (Model number G2762A) was used to characterize the vapor compositions. Two columns were dedicated to different gases: column A, MS-5A 10m, was used for compressed gases such as He, $H_2$ and light vapor molecules and column B was used for compressed gases, such as $CO_2$, $N_2$ and light hydrocarbons.

The hollow fiber modules were fabricated by potting the fibers inside polycarbonate tubes with an active length of 36.8 cm. The inner diameters of the tubes were about 0.5 inch (1.27 cm). The detailed fiber and module parameters are summarized in Table 1. Five types of fibers with the pore size ranging from 0.04 to 30 μm, and the wall thickness from 30 to 440 μm were selected for the evaluation tests. Module fibers used in this experiment were procured from Setec, Inc. (Module-2), Pall company (Module-3), Spectrumlab (Module-4 and Module-9), and Celgard® fiber company (Module-6).

The mass transfer area per unit volume ranged from 1094 to 1473 $m^2/m^3$, which was calculated based on the outside surface area of hollow fibers. Comparing to Sulzer Chemtech® 250 and 500 structured packing materials, the mass transfer area is about 4 to 6 times larger. The packing density ranged from 11-45%. Note that the across area ratio ($A_g/A_L$) of vapor to liquid defines the open area between vapor and liquid to flow within column.

Five trials, and, thus, five differing hollow fiber modules were tested under total reflux conditions, were conducted using the setup in FIG. 7. An olefinic/paraffinic mixture of ~30% propane and 70% propylene mole percent was used as the starting material. During the experiments, the concentration of propane and propylene changes within 10%, thus the slope of their equilibrium line is almost constant. Therefore, the NTU was determined from the measured propylene compositions at the top and the bottom of the column.

Figure 8A:
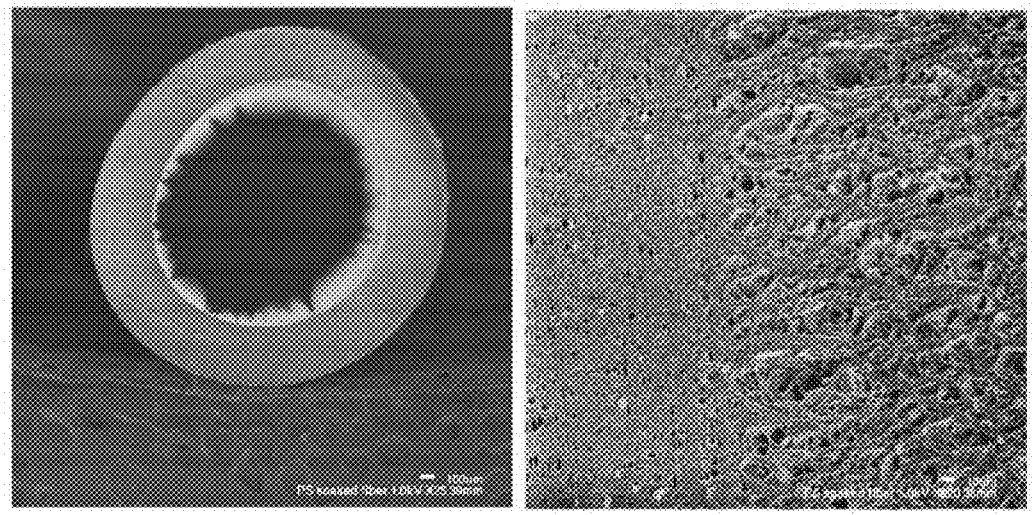
FIG. 8a shows a scanning electron microscope image detailing the morphology of the porous materials used in Module-2.
Figure 8B:
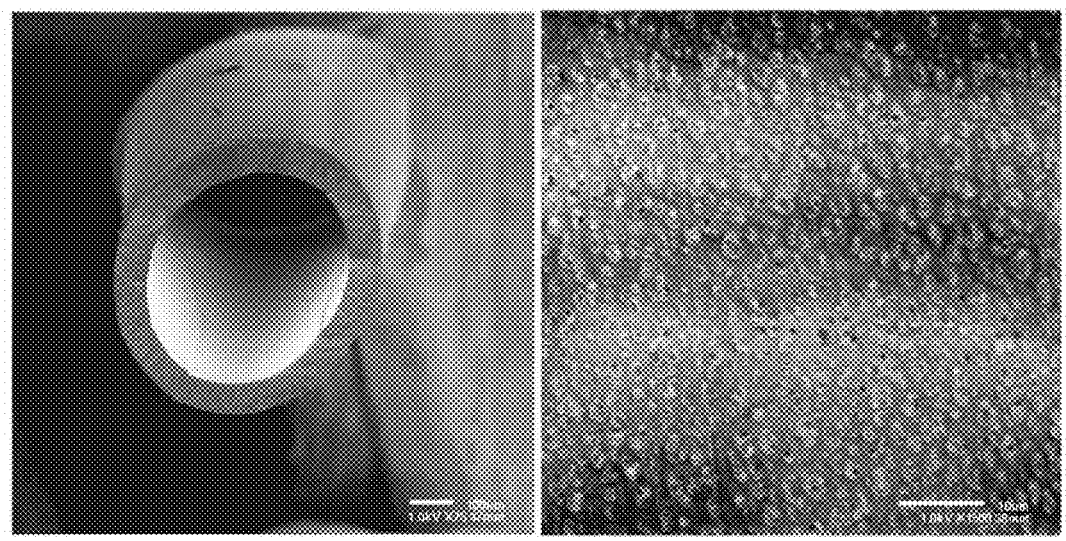
FIG. 8b shows a scanning electron microscope image detailing the morphology of the porous materials used in Module-4.

FIGS. 8a and 8b show the scanning electron microscope (SEM) images of the polypropylene fiber used in Module-2 module and polysulfone fiber used in Module-4 module, respectively.

Figure 9:
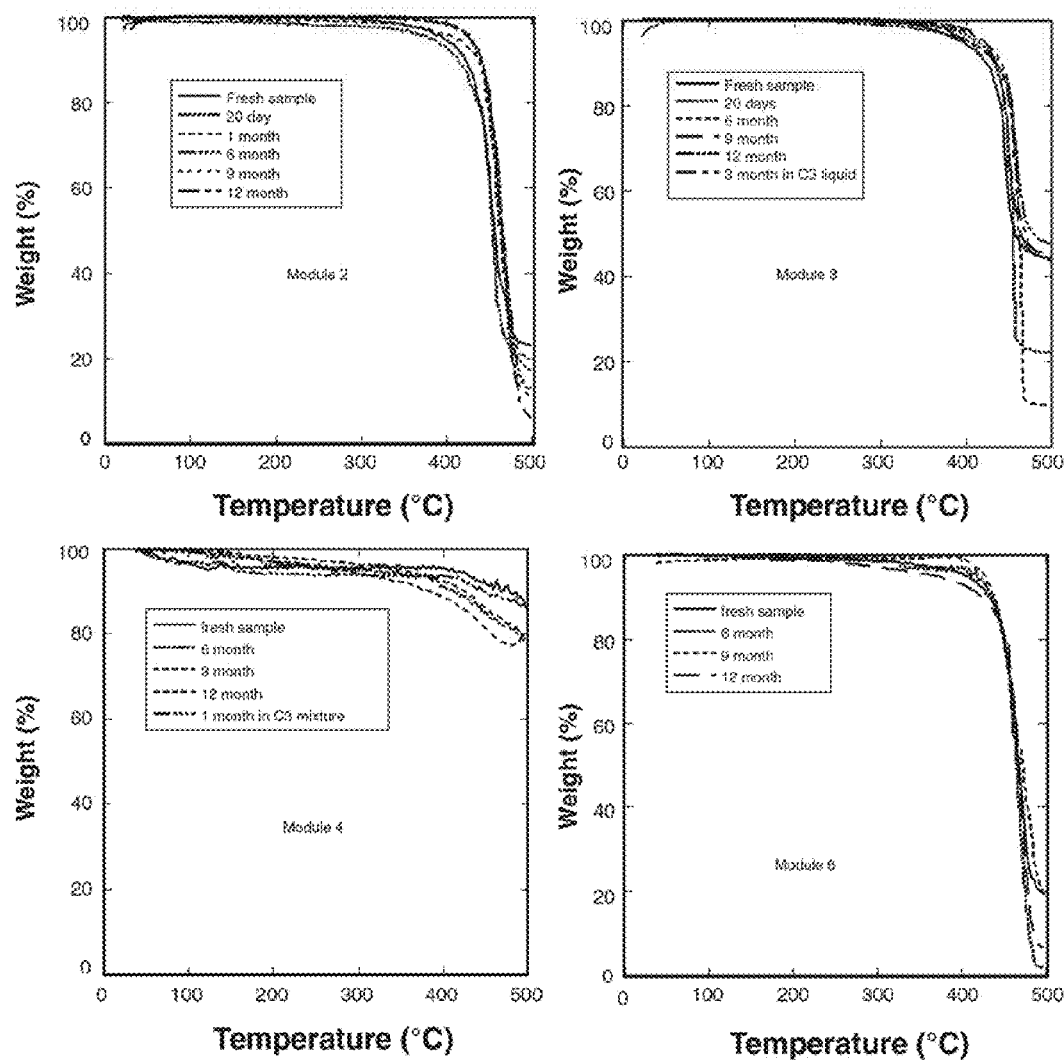
FIG. 9 graphically shows the thermogravimetry analysis (TGA) results of several hollow fiber samples tested in LANL modules.

A thermogravimetry analysis (TGA) was used to test the stability of the hollow fiber samples in all the modules. The TGA results for these aged fiber samples are shown in FIG. 9. The TGA results show that the weight percent (W %) change over time is almost identical for each fiber sample, concluding that all of these fibers samples are stable after they were soaked in pentane at room temperature for one year. Several hollow fiber samples were tested in olefin and paraffin mixture for several months with the corresponding TGA results essentially the same as the results obtained from samples soaked in pentane, indicating that pentane can be used as surrogate solvent to test the hollow fibers.

Figure 10:
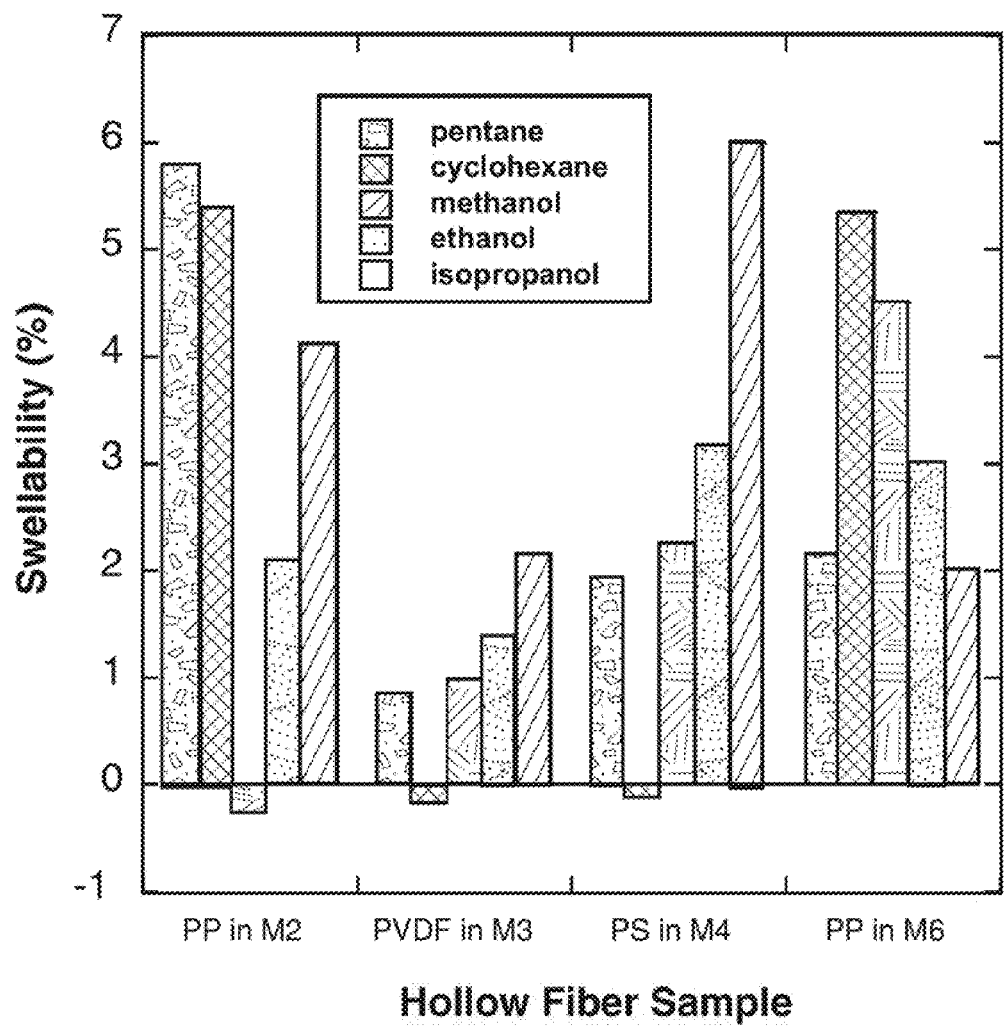
FIG. 10 graphically shows the swellability test results of hollow fiber samples in hollow fiber modules.

The material characteristic of minimum swellability is preferred in fiber material in order to minimize geometry change during operation. Thus, the swellability of the fiber modules has been tested in several organic solvents as well. The tested results, shown in FIG. 10, indicate the swellability of these fibers was less than 10% in all tested solvents. Based on observation of liquid flow down the fibers while using pentane as the solvent, it is apparent that all of the fibers are easily wetted with light hydrocarbon materials.

Figure 11:
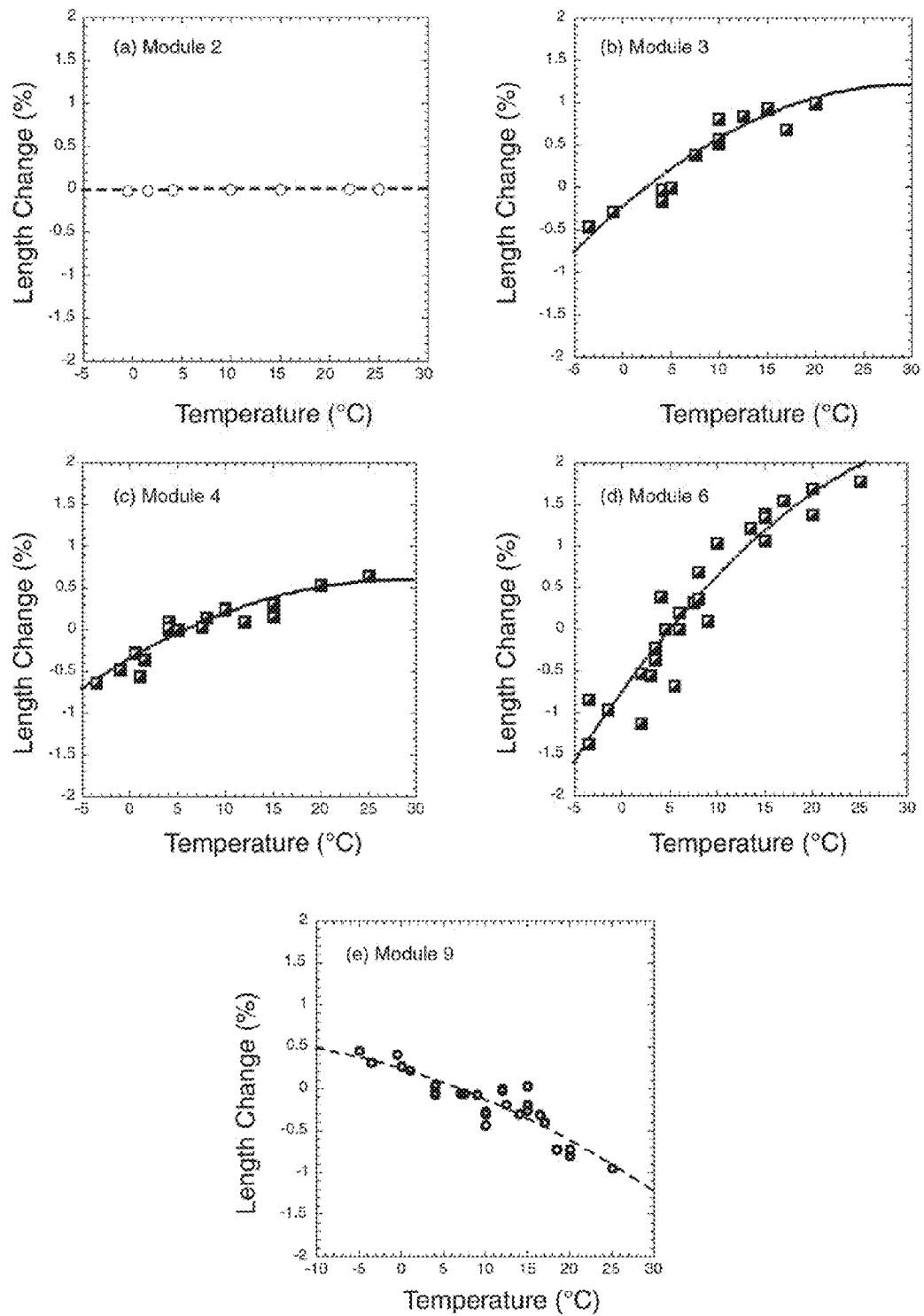
FIG. 11 graphically shows the effect of temperature on the length change of hollow fiber samples.

Referring to FIG. 11, once the hollow fibers were soaked in pentane, the temperature effect on the change in length of the hollow fibers, and, therefore on separation performance was negligible. All of these results prove that the thermal stability of these hollow fibers is suitable to the distillation application for organic solvents.

Figure 12:
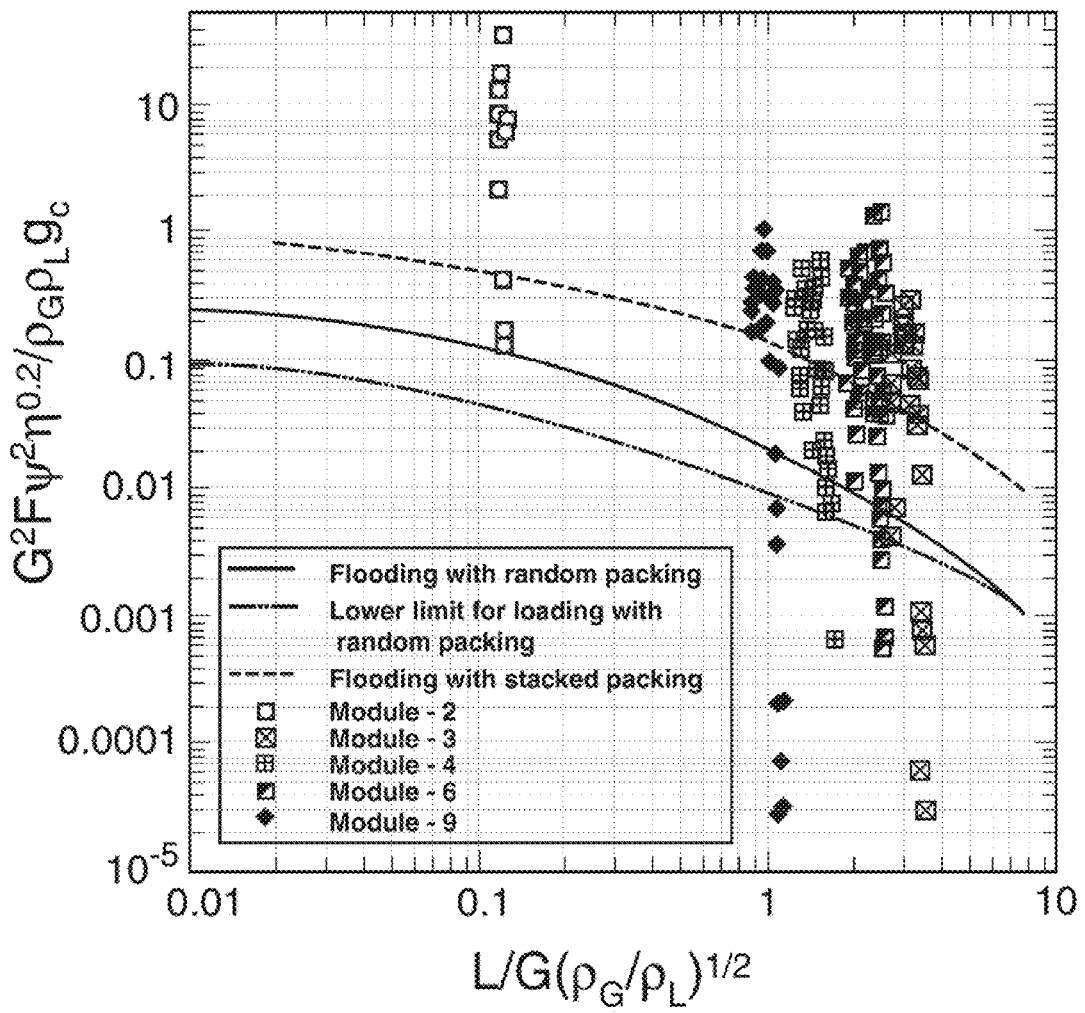
FIG. 12 graphically shows flow parameter vs. flow capacity.

FIG. 12 is a plot of flow parameter vs flow capacity for the tested modules shown in Table 1. The plot demonstrates that a column (or module) including porous tubes in hollow fiber form can handle a wide range of flow conditions. These flow conditions are at least 100 times larger than the flooding limit of conventional packing materials. Further, the tested modules operated below the loading line of conventional packing materials. This proves that the tube-shell configuration of porous materials in a distillation column can provide separate channels for vapor and liquid to prevent flooding and loading

TABLE 1

A summary of module hollow fiber parameters

|  | Module - 2 | Module - 3 | Module - 4 | Module - 6 | Module - 9 |
| --- | --- | --- | --- | --- | --- |
| Fiber material | Polypropylene | Polyvinylididene Fluoride | Polysulfone | Polypropylene | Mixed Ester |
| Pore size (μm) | 0.1-30 | <0.02 | 0.05-0.5 | 0.04 | 0.1-1.0 |
| Fiber ID (mm) | 1.74 | 0.626 | 0.480 | 0.240 | 0.680 |
| Fiber OD (mm) | 2.62 | 1.20 | 0.630 | 0.300 | 0.850 |
| Thickness (μm) | 440 | 288 | 75 | 30 | 85 |
| Number of fibers | 19 | 20 | 70 | 198 | 47 |
| Packing density (%) | 45 | 17 | 17 | 11 | 22 |
| Packing factor ($ft^{-1}$) | 2287 | 327.7 | 587 | 637 | 873 |
| $A_g/A_L$ | 0.55 | 17.1 | 8.28 | 12.56 | 5.64 |
| a ($cm^2/cm^3$) | 12.35 | 5.95 | 10.94 | 14.73 | 13.39 | problems, and at the same time provide a preferred large contact area between the vapor and liquid.

The separation performance of these modules is summarized in Table 2. The HETP value determined from the Module-2 module was 3.0 inch (7.6 cm), indicating a mass transfer time as low as ~0.40 sec, which was the best mass transfer rate of all the modules tested. Thus, these results prove that hollow fiber materials can be used as structured packing materials in olefin/paraffin distillation separation. It is worthy to note that among these modules, Module-3 has the worst performance (meaning larger mass transfer time). This poor performance is due to the fibers packed in Module-3 having much smaller pore sizes (0.02 μm) and a large wall thickness (~288 μm).

The dense morphology creates a greater resistance layer between liquid and vapor, thereby reducing both the heat and mass transfer rate between the two phases. This observation again proves that the large and/or open porous structure inside the membrane wall is critical to allow the process liquid to easily flow across the membrane under a small driving force (<0.5 psi) and to interact with the vapor phase promoting heat and mass transfer.

Note that the comparatively poor separation performance of Module-3 still provided a mass transfer time of less than 40 seconds. Whereas, for the Sulzer Chemtech® series packing materials, the mass transfer time is greater than 40 seconds (reference: "Non-selective membrane for separations", E. L. Cussler, Journal of Chem. Tech. and Biotech, 78, 98-102).

TABLE 2

Summary of separation performance of tested modules

|  | Module-2 | Module-3 | Module-4 | Module-6 | Module-9 |
|---|---|---|---|---|---|
| Module temp (° C.) | 24.3 | 21.1 | 17.6 | 19.7 | 17.5 |
| System pressure (Psig) | 151.3 | 140.4 | 124.9 | 131.7 | 124.0 |
| Liquid flowrate (g/min) | 8.0 | 4.67 | 4.12 | 11.2 | 11.2 |
| Vapor velocity $V_g$ (cm/sec) | 22.26 | 3.36 | 3.36 | 8.02 | 9.87 |
| $C_3^=$ (Top of module) | 86.0 | 72.6 | 75.1 | 76.9 | 75.0 |
| $C_3^=$ (Bottom of module) | 79.0 | 71.3 | 71.7 | 70.4 | 70.0 |
| NTU | 4.5 | 0.65 | 1.53 | 2.63 | 2.00 |
| HTU (cm) | 8.2 | 56.6 | 24.2 | 13.9 | 18.4 |
| HEPT (cm) | 10.5 | 68.8 | 29.4 | 16.9 | 22.4 |
| Mass transfer coeff - $K_G$ (cm/sec) | 0.224 | 0.010 | 0.013 | 0.041 | 0.040 |
| Mass transfer area (a) (cm$^2$/cm$^3$) | 12.35 | 5.95 | 10.94 | 14.73 | 13.39 |
| Mass transfer time $1/(K_G \cdot a)$ (sec) | 0.37 | 16.8 | 7.18 | 1.73 | 1.86 |

In distillation processes, as the temperature increases, the relative volatility increases favoring separation. However, the density ratio between the liquid and vapor for propane and propylene increase from 22 to 46 as the temperature decreases from 25 to 0° C., and so disengagement of liquid and vapor becomes easier in the lower temperature range.

Figure 13:
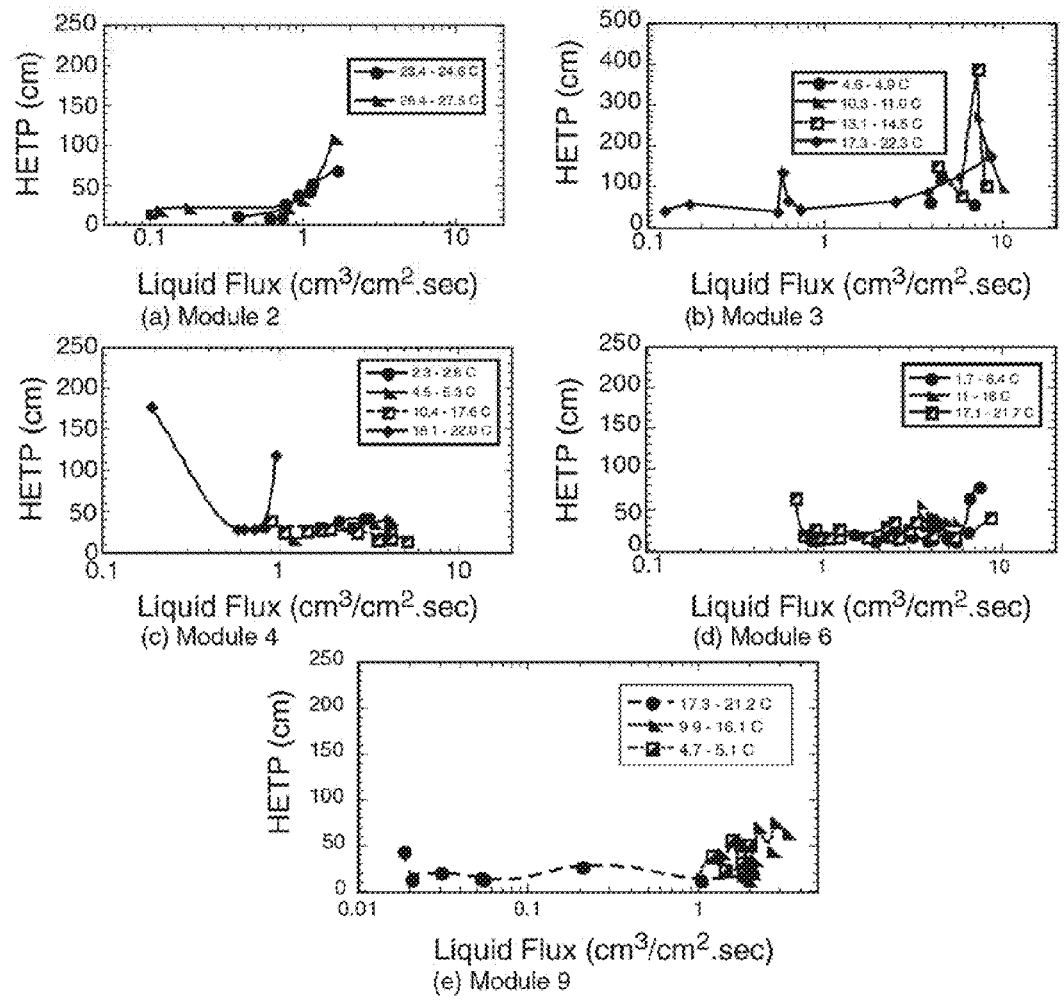
FIG. 13 graphically shows the effect of temperature and fluid capacity on the separation efficiency of hollow fiber modules.
Figure 14:
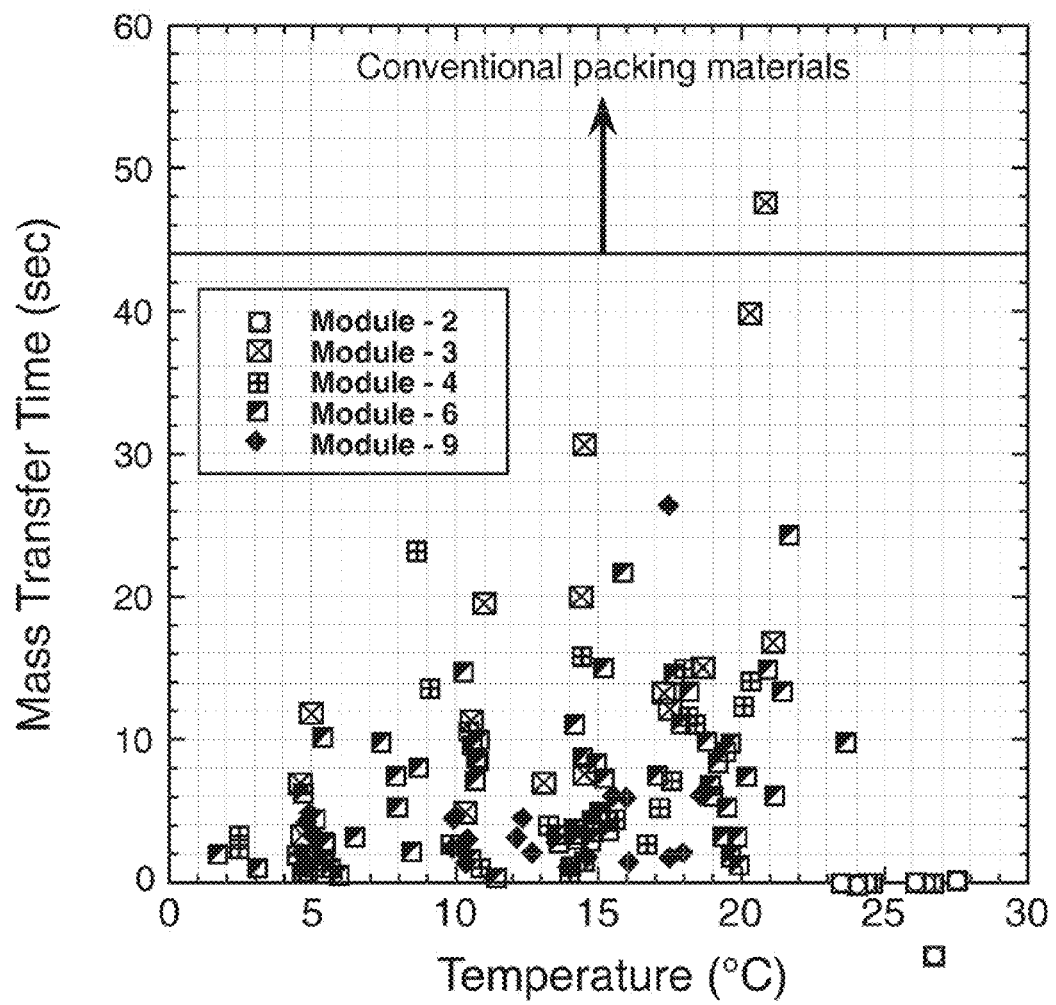
FIG. 14 graphically shows the effect of operation temperature on the mass transfer time obtained from hollow fiber modules for the propylene/propane separation.

In order to explore the effect of temperature on the separation performance, a series of experiments was conducted over a temperature range from 0 to 25° C. for the previously mentioned modules. Referring to FIG. 13, the experimental results proved that higher separation efficiency was achieved at lower temperatures. The HETP remains low (<40 cm) for a large liquid flux range (>200 cm$^3$/cm$^3$-sec) for both Module-4 and Module-6. Note that when the operation temperature was less than 6° C., the mass transfer time ($1/K_G \cdot a$) was typically less than 10 seconds, which is at least 5 times better than the conventional packing materials (see FIG. 14).

Historically, the separation of propylene and propane has been a difficult separation for the petrochemical industry. This is due in part to the narrow boiling point difference between propylene and propane at ambient conditions, which is only 7.5° C. The relative volatility is less than 1.2 when the temperature is close to 0° C. A 1° C. temperature difference along the column for a propylene/propane (70/30) mixture can result in ~15% propylene concentration difference. However, due to the largely open structure in the conventional packing materials, convective heat transfer between liquid and vapor is large, making it difficult to maintain a couple of degrees temperature gradient within a short distance (<50 cm).

Figure 15:
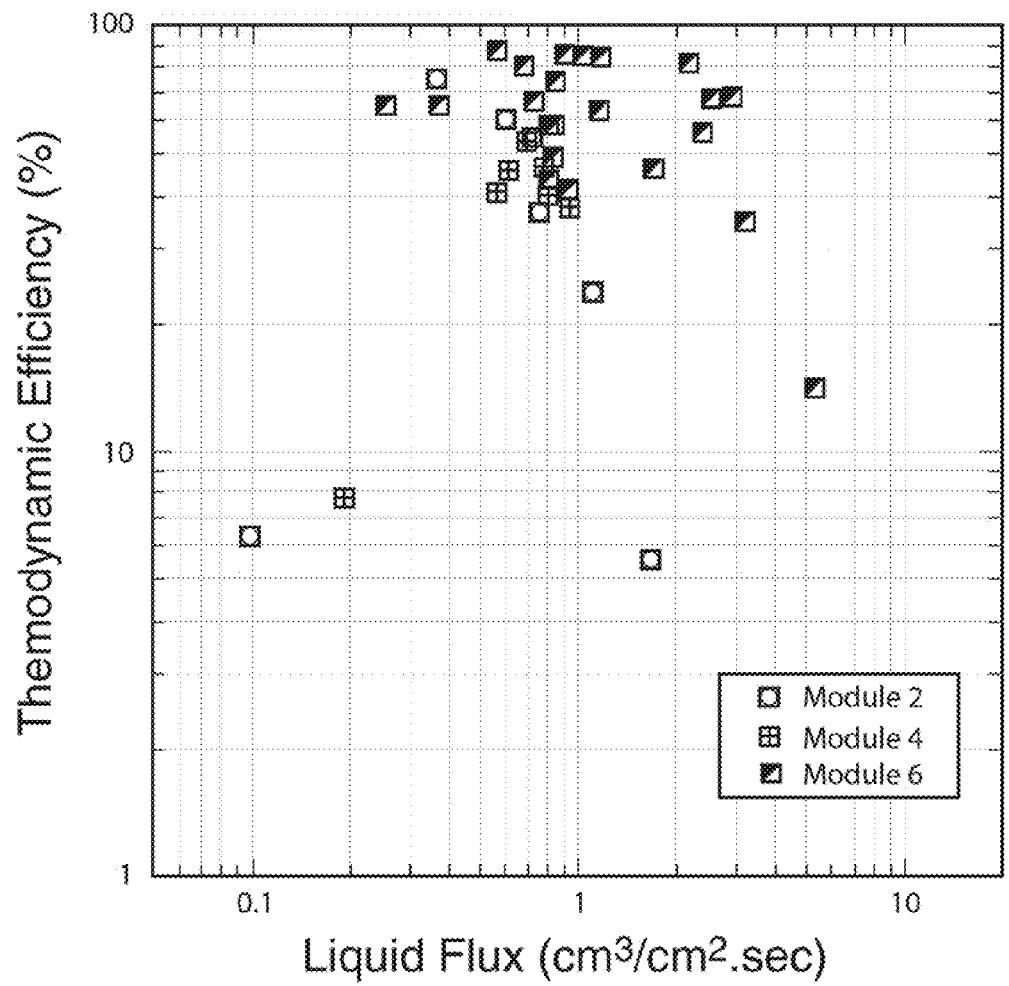
FIG. 15 graphically shows the column separation efficiency for Modules 2, 4, and 6.

On the contrary, due to the confined diameter of the hollow fibers inside dimension and meso/microporous structure on the wall, the liquid flow is typically in the laminar flow region. Thus, the convection among the fluids is largely decreased making larger temperature gradients within short distances possible. Thus, a small HETP (or HTU) is expected. The thermodynamic efficiency is typically larger than 85% when the modules are operated at their optimized operation zone (see FIG. 15).

Theoretically, when the liquid flow slows down, convection between the two phases is reduced and high separation efficiency is expected. However, at very low flows, an uneven liquid film on the surface of the packing materials can occur. This can be the result of insufficient liquid to cover the surface area of the packing material or channeling of liquid flow. Thus, the reduced liquid surface area results in less efficient mass transfer.

However, with the present invention, utilization of porous tube materials, such as mesoporous and microporous hollow fibers, provides a pore size on the liquid side of wall that is less than a few micrometers, but includes a wall thickness with the same order of magnitude as the tubes inside diameter (from about ten micrometers to a few hundred micrometers) (see FIG. 8a). Thus, the liquid in the liquid phase is uniformly distributed into the tube while the liquid thin film forms on the wall of the pores and/or the outer surface.

Due to a much thinner and uniform film formed on the surface of the porous materials, the total amount of liquid required to cover the surface of porous materials is much less than that required to cover the surface of conventional packing materials. Therefore, when the liquid loading drops below the loading line (dashed line) in FIG. 12, the modules were able to maintain their separation efficiency.

The present invention provides more surface area and a more uniform distribution of liquid per unit volume of material than conventional materials, and, thus, correspondingly yields enhanced mass transfer per unit of volume. For example, referring to FIG. 13 for Module-2, when the liquid flow is below 2.5 g/min (<0.1 cm$^3$/cm$^2$·sec), the HETP is still below 15 cm (<6 inch). These results cannot be achieved through the use of conventional packing materials.

In summary, the present invention is a porous tube material that may be used as structured packing in a distillation process that provides a larger process flow rate operating range than current conventional packing materials. The present invention provides for an HETP of less than 10 cm and mass transfer time less than 1 second. A wide range of materials may be used as the porous tube material, to include ceramics, metals, and polymers. Therefore, the operational ranges of distillations systems using these materials can cover temperatures from about −60° C. to 200° C., and pressures from a few psig to several hundred psig. Thus, any type of distillation process within these parameters may be performed with the present invention, to include separation of light hydrocarbons such as olefin and paraffin.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for enriching a light hydrocarbon mixture that includes propylene and propane, comprising:

providing a vertically oriented distillation column having a bottom and a top, the distillation column having an entrance for vapor near the bottom of the distillation column and an exit for vapor near the top of the distillation column, the distillation column comprising a plurality of tubular membranes bundled in a parallel configuration, the tubular membranes being non-selective and having porous walls and a lumen, the porous walls capable of being wetted throughout by light hydrocarbon liquid, sending vapor of the light hydrocarbon mixture into the entrance and then upward through the distillation column and then through the exit, condensing vapor that exits to form a liquid, the liquid being enriched in propylene compared to the vapor that is sent through the entrance near the bottom of the distillation column sending at least a portion of the liquid that forms from the condensed vapor into the lumen of the tubular membranes at the top of the column wherein the liquid flows downward through the lumen of the tubular membranes while vapor continues to flow countercurrently upward through spaces in between the tubular membranes but not through the lumen, whereby an interface between vapor and liquid forms in the porous walls, wherein vapor near the top of the column becomes enriched in propylene and liquid near the bottom of the column becomes enriched in propane.

* * * * *